(12) United States Patent
Albani et al.

(10) Patent No.: US 7,790,158 B2
(45) Date of Patent: Sep. 7, 2010

(54) METHODS FOR EPITOPE-SPECIFIC AND CYTOKINE/ANTICYTOKINE COMBINATION IMMUNOTHERAPIES

(75) Inventors: Salvatore Albani, Encinitas, CA (US); Alberto Martini, Piacenza (IT)

(73) Assignee: The Regents of the University of California, Oakland, CA (US)

( * ) Notice: Subject to any disclaimer, the term of this patent is extended or adjusted under 35 U.S.C. 154(b) by 1243 days.

(21) Appl. No.: 10/490,949

(22) PCT Filed: Sep. 25, 2002

(86) PCT No.: PCT/US02/30578

§ 371 (c)(1), (2), (4) Date: Oct. 20, 2005

(87) PCT Pub. No.: WO03/026579

PCT Pub. Date: Apr. 3, 2003

(65) Prior Publication Data

US 2006/0093574 A1    May 4, 2006

(51) Int. Cl.
*A61K 38/19* (2006.01)
*A61K 39/395* (2006.01)

(52) U.S. Cl. .................................. 424/130.1; 514/2
(58) Field of Classification Search .............. None
See application file for complete search history.

(56) References Cited

U.S. PATENT DOCUMENTS

| | | | |
|---|---|---|---|
| 5,968,524 A * | 10/1999 | Watson et al. ............. | 424/248.1 |
| 6,037,135 A | 3/2000 | Kubo et al. | |
| 6,077,519 A | 6/2000 | Storkus et al. | |
| 6,218,371 B1 | 4/2001 | Krieg et al. | |

| | | | |
|---|---|---|---|
| 2001/0007758 A1 | 7/2001 | Weiner et al. | |

FOREIGN PATENT DOCUMENTS

| WO | WO 9857659 A1 * | 12/1998 |
|---|---|---|
| WO | WO 00/23053 | 4/2000 |

OTHER PUBLICATIONS

Seymour et al: "Anti-TNF agents for rheumatoid arthritis" Br J Clin Pharmacol. Mar. 2001;51(3):201-8.
Prakken et al: "Peptide-induced nasal tolerance for a mycobacterial heat shock protein 60 T cell epitope in rats suppresses both adjuvant arthritis and nonmicrobially induced experimental arthritis," Proc Natl Acad Sci U S A. Apr. 1, 1997;94(7):3284-9.
Charo et al: "DNA immunization of HLA transgenic mice with a plasmid expressing mycobacterial heat shock protein 65 results in HLA class I- and II-restricted T cell responses that can be augmented by cytokines" Hum Gene Ther. Sep. 20, 2001;12(14):1797-804.
Prakken et al: "Inhibition of adjuvant-induced arthritis by interleukin-10-driven regulatory cells induced via nasal administration of a peptide analog of an arthritis-related heat-shock protein 60 T cell epitope," Arthritis Rheum. Jul. 2002;46(7):1937-46.
Roord et al: "Modulation of T cell function by combination of epitope specific and low dose anticytokine therapy controls autoimmune arthritis," PLOS One. Dec. 20, 2006;1:e87.
International Search Report of PCT/US2002/030578.
Supplemental European Search Report of EP02773596.8.

* cited by examiner

*Primary Examiner*—Michael Pak
(74) *Attorney, Agent, or Firm*—DLA Piper LLP (US)

(57) ABSTRACT

The current invention provides for methods of immunotherapy using a combination of epitope-specific and cytokine or anticytokine immunotherapy. The method provides for modulation of pathogenic immune responses and includes the identification of molecules comprising specific epitopes involved in a particular disease state of interest, administration of the epitope-specific molecule in conjunction with the cytokine or anticytokine, and downstream modification of the administration of the cytokine/anticytokine relative to the administration of the epitope-specific molecule.

17 Claims, 7 Drawing Sheets

Proliferation after *in vitro* stimulation of mandibular lymphnode cells (MLN)

SEQUENCE LISTING

<160> NUMBER OF SEQ ID NOS: 59

<210> SEQ ID NO 1
<211> LENGTH: 15
<212> TYPE: PRT
<213> ORGANISM: Escherichia coli

<400> SEQUENCE: 1

Val Leu Thr Asp Ser Gln Lys Arg Ala Ala Tyr Asp Gln Tyr Gly
1               5                   10                  15

<210> SEQ ID NO 2
<211> LENGTH: 15
<212> TYPE: PRT
<213> ORGANISM: Escherichia coli

<400> SEQUENCE: 2

Gln Asp Tyr Tyr Glu Ile Leu Gly Val Ser Lys Thr Ala Glu Glu
1               5                   10                  15

<210> SEQ ID NO 3
<211> LENGTH: 15
<212> TYPE: PRT
<213> ORGANISM: Escherichia coli

<400> SEQUENCE: 3

Arg Lys Ala Tyr Lys Arg Leu Ala Met Lys Tyr His Pro Asp Arg
1               5                   10                  15

<210> SEQ ID NO 4
<211> LENGTH: 16
<212> TYPE: PRT
<213> ORGANISM: Escherichia coli

<400> SEQUENCE: 4

Gln Lys Arg Ala Ala Tyr Asp Gln Tyr Gly His Ala Ala Phe Glu Gln
1               5                   10                  15

<210> SEQ ID NO 5
<211> LENGTH: 15
<212> TYPE: PRT
<213> ORGANISM: Escherichia coli

<400> SEQUENCE: 5

Gln Gly Phe Phe Ala Val Gln Gln Thr Cys Pro His Cys Gln Gly
1               5                   10                  15

<210> SEQ ID NO 6
<211> LENGTH: 15
<212> TYPE: PRT
<213> ORGANISM: Escherichia coli

<400> SEQUENCE: 6

Ser Lys Thr Leu Ser Val Lys Ile Pro Gly Ala Val Asp Thr Gly
1               5                   10                  15

<210> SEQ ID NO 7
<211> LENGTH: 15
<212> TYPE: PRT
<213> ORGANISM: Escherichia coli

<400> SEQUENCE: 7

Gly Asp Leu Tyr Val Gln Val Gln Val Lys Gln His Pro Ile Phe

-continued

```
1               5                   10                  15

<210> SEQ ID NO 8
<211> LENGTH: 15
<212> TYPE: PRT
<213> ORGANISM: Escherichia coli

<400> SEQUENCE: 8

Tyr Cys Glu Val Pro Ile Asn Phe Ala Met Ala Ala Leu Gly Gly
1               5                   10                  15

<210> SEQ ID NO 9
<211> LENGTH: 15
<212> TYPE: PRT
<213> ORGANISM: Escherichia coli

<400> SEQUENCE: 9

Pro Ile Asn Phe Ala Met Ala Ala Leu Gly Gly Glu Ile Glu Val
1               5                   10                  15

<210> SEQ ID NO 10
<211> LENGTH: 15
<212> TYPE: PRT
<213> ORGANISM: Escherichia coli

<400> SEQUENCE: 10

Gln Lys Arg Ala Ala Tyr Asp Gln Tyr Gly His Ala Ala Phe Glu
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: E. Coli mutant sequence

<400> SEQUENCE: 11

Asp Glu Arg Ala Ala Tyr Asp Gln Tyr Gly His Ala Ala Phe Glu
1               5                   10                  15

<210> SEQ ID NO 12
<211> LENGTH: 15
<212> TYPE: PRT
<213> ORGANISM: Escherichia coli

<400> SEQUENCE: 12

Ala Val Glu Leu Glu Ser Pro Phe Ile Leu Leu Ala Asp Lys Lys
1               5                   10                  15

<210> SEQ ID NO 13
<211> LENGTH: 15
<212> TYPE: PRT
<213> ORGANISM: Escherichia coli

<400> SEQUENCE: 13

Pro Phe Ile Leu Leu Ala Asp Lys Lys Ile Ser Asn Ile Arg Glu
1               5                   10                  15

<210> SEQ ID NO 14
<211> LENGTH: 15
<212> TYPE: PRT
<213> ORGANISM: Escherichia coli

<400> SEQUENCE: 14

Gly Glu Ala Leu Ala Thr Leu Val Val Asn Thr Met Arg Gly Ile
```

```
1               5                   10                  15
```

<210> SEQ ID NO 15
<211> LENGTH: 15
<212> TYPE: PRT
<213> ORGANISM: Escherichia coli

<400> SEQUENCE: 15

```
Val Ala Gly Leu Met Ile Thr Thr Glu Cys Met Val Thr Asp Leu
1               5                   10                  15
```

<210> SEQ ID NO 16
<211> LENGTH: 15
<212> TYPE: PRT
<213> ORGANISM: Homo sapiens

<400> SEQUENCE: 16

```
Gln Lys Arg Ala Ala Val Asp Thr Tyr Cys Arg His Asn Tyr Gly
1               5                   10                  15
```

<210> SEQ ID NO 17
<211> LENGTH: 15
<212> TYPE: PRT
<213> ORGANISM: Homo sapiens

<400> SEQUENCE: 17

```
Lys Asp Leu Leu Glu Gln Lys Arg Ala Ala Val Asp Thr Tyr Cys
1               5                   10                  15
```

<210> SEQ ID NO 18
<211> LENGTH: 15
<212> TYPE: PRT
<213> ORGANISM: Homo sapiens

<400> SEQUENCE: 18

```
Ala Ser Tyr Tyr Glu Ile Leu Asp Val Pro Arg Ser Ala Ser Ala
1               5                   10                  15
```

<210> SEQ ID NO 19
<211> LENGTH: 15
<212> TYPE: PRT
<213> ORGANISM: Homo sapiens

<400> SEQUENCE: 19

```
Lys Asp Tyr Tyr Gln Thr Leu Gly Leu Ala Arg Gly Ala Ser Asp
1               5                   10                  15
```

<210> SEQ ID NO 20
<211> LENGTH: 15
<212> TYPE: PRT
<213> ORGANISM: Homo sapiens

<400> SEQUENCE: 20

```
Thr Thr Tyr Tyr Asp Val Leu Gly Val Lys Pro Asn Ala Thr Gln
1               5                   10                  15
```

<210> SEQ ID NO 21
<211> LENGTH: 15
<212> TYPE: PRT
<213> ORGANISM: Homo sapiens

<400> SEQUENCE: 21

```
Lys Lys Ala Tyr Arg Arg Lys Ala Leu Gln Trp His Pro Asp Lys
1               5                   10                  15
```

```
<210> SEQ ID NO 22
<211> LENGTH: 15
<212> TYPE: PRT
<213> ORGANISM: Homo sapiens

<400> SEQUENCE: 22

Lys Arg Ala Tyr Arg Arg Gln Ala Leu Arg Tyr His Pro Asp Lys
1               5                   10                  15

<210> SEQ ID NO 23
<211> LENGTH: 15
<212> TYPE: PRT
<213> ORGANISM: Homo sapiens

<400> SEQUENCE: 23

Lys Lys Ala Tyr Arg Lys Leu Ala Leu Lys Tyr His Pro Asp Lys
1               5                   10                  15

<210> SEQ ID NO 24
<211> LENGTH: 15
<212> TYPE: PRT
<213> ORGANISM: Homo sapiens

<400> SEQUENCE: 24

Phe Arg Ser Val Ser Thr Ser Thr Thr Phe Val Gln Gly Arg Arg
1               5                   10                  15

<210> SEQ ID NO 25
<211> LENGTH: 15
<212> TYPE: PRT
<213> ORGANISM: Homo sapiens

<400> SEQUENCE: 25

Pro Gly Met Val Gln Gln Ile Gln Ser Val Cys Met Glu Cys Gln
1               5                   10                  15

<210> SEQ ID NO 26
<211> LENGTH: 15
<212> TYPE: PRT
<213> ORGANISM: Homo sapiens

<400> SEQUENCE: 26

Gly Arg Arg Ile Thr Thr Arg Arg Ile Met Glu Asn Gly Gln Glu
1               5                   10                  15

<210> SEQ ID NO 27
<211> LENGTH: 16
<212> TYPE: PRT
<213> ORGANISM: Homo sapiens

<400> SEQUENCE: 27

Gln Ala Tyr Glu Val Leu Ser Asp Ala Lys Lys Arg Glu Leu Tyr Asp
1               5                   10                  15

<210> SEQ ID NO 28
<211> LENGTH: 16
<212> TYPE: PRT
<213> ORGANISM: Homo sapiens

<400> SEQUENCE: 28

Glu Ala Tyr Glu Val Leu Ser Asp Lys His Lys Arg Glu Ile Tyr Asp
1               5                   10                  15

<210> SEQ ID NO 29
```

```
<211> LENGTH: 15
<212> TYPE: PRT
<213> ORGANISM: Homo sapiens

<400> SEQUENCE: 29

Ser Gly Pro Phe Phe Thr Phe Ser Ser Phe Pro Gly His Ser
1               5                   10                  15

<210> SEQ ID NO 30
<211> LENGTH: 15
<212> TYPE: PRT
<213> ORGANISM: Homo sapiens

<400> SEQUENCE: 30

Asp Gly Gln Leu Lys Ser Val Thr Ile Asn Gly Val Pro Asp Asp
1               5                   10                  15

<210> SEQ ID NO 31
<211> LENGTH: 15
<212> TYPE: PRT
<213> ORGANISM: Homo sapiens

<400> SEQUENCE: 31

Asp Leu Gln Leu Ala Met Ala Tyr Ser Leu Ser Glu Met Glu Ala
1               5                   10                  15

<210> SEQ ID NO 32
<211> LENGTH: 15
<212> TYPE: PRT
<213> ORGANISM: Homo sapiens

<400> SEQUENCE: 32

Glu Asp Leu Phe Met Cys Met Asp Ile Gln Leu Val Glu Ala Leu
1               5                   10                  15

<210> SEQ ID NO 33
<211> LENGTH: 15
<212> TYPE: PRT
<213> ORGANISM: Homo sapiens

<400> SEQUENCE: 33

Leu Cys Gly Phe Gln Lys Pro Ile Ser Thr Leu Asp Asn Arg Thr
1               5                   10                  15

<210> SEQ ID NO 34
<211> LENGTH: 15
<212> TYPE: PRT
<213> ORGANISM: Homo sapiens

<400> SEQUENCE: 34

Arg Thr Ile Val Ile Thr Ser His Pro Gly Gln Ile Val Lys His
1               5                   10                  15

<210> SEQ ID NO 35
<211> LENGTH: 15
<212> TYPE: PRT
<213> ORGANISM: Homo sapiens

<400> SEQUENCE: 35

Gly Arg Leu Ile Ile Glu Phe Lys Val Asn Phe Pro Glu Asn Gly
1               5                   10                  15

<210> SEQ ID NO 36
<211> LENGTH: 23
<212> TYPE: PRT
```

<213> ORGANISM: Homo sapiens

<400> SEQUENCE: 36

Thr Asn Glu Glu Ala Gly Asp Gly Thr Thr Thr Ala Thr Val Leu Ala
1               5                   10                  15
Arg Ser Ile Ala Lys Glu Gly
            20

<210> SEQ ID NO 37
<211> LENGTH: 32
<212> TYPE: PRT
<213> ORGANISM: Homo sapiens

<400> SEQUENCE: 37

Arg Lys Gly Val Ile Thr Val Lys Asp Gly Lys Thr Leu Asn Asp Glu
1               5                   10                  15
Leu Glu Ile Ile Glu Gly Met Lys Phe Asp Arg Gly Tyr Ile Ser Pro
            20                  25                  30

<210> SEQ ID NO 38
<211> LENGTH: 33
<212> TYPE: PRT
<213> ORGANISM: Homo sapiens

<400> SEQUENCE: 38

Gly Gln Lys Cys Glu Phe Gln Asp Ala Tyr Val Leu Leu Ser Glu Lys
1               5                   10                  15
Lys Ile Ser Ser Ile Gln Ser Ile Val Pro Ala Leu Glu Ile Ala Asn
            20                  25                  30
Ala

<210> SEQ ID NO 39
<211> LENGTH: 15
<212> TYPE: PRT
<213> ORGANISM: Homo sapiens

<400> SEQUENCE: 39

Lys Cys Glu Phe Gln Asp Ala Tyr Val Leu Leu Ser Glu Lys Lys
1               5                   10                  15

<210> SEQ ID NO 40
<211> LENGTH: 15
<212> TYPE: PRT
<213> ORGANISM: Homo sapiens

<400> SEQUENCE: 40

Ala Tyr Val Leu Leu Ser Glu Lys Lys Ile Ser Ser Ile Gln Ser
1               5                   10                  15

<210> SEQ ID NO 41
<211> LENGTH: 39
<212> TYPE: PRT
<213> ORGANISM: Homo sapiens

<400> SEQUENCE: 41

Lys Pro Leu Val Ile Ile Ala Glu Asp Val Asp Gly Glu Ala Leu Ser
1               5                   10                  15
Thr Leu Val Leu Asn Arg Leu Lys Val Gly Leu Gln Val Val Ala Val
            20                  25                  30
Lys Ala Pro Gly Phe Gly Asp
            35

```
<210> SEQ ID NO 42
<211> LENGTH: 16
<212> TYPE: PRT
<213> ORGANISM: Homo sapiens

<400> SEQUENCE: 42

Gly Glu Ala Leu Ser Thr Val Leu Val Leu Asn Arg Leu Lys Val Gly
1               5                   10                  15

<210> SEQ ID NO 43
<211> LENGTH: 36
<212> TYPE: PRT
<213> ORGANISM: Homo sapiens

<400> SEQUENCE: 43

Ser Asp Val Glu Val Asn Glu Lys Lys Asp Arg Val Thr Asp Ala Leu
1               5                   10                  15

Asn Ala Thr Arg Ala Ala Val Glu Glu Gly Ile Val Leu Gly Gly Gly
                20                  25                  30

Cys Ala Leu Leu
        35

<210> SEQ ID NO 44
<211> LENGTH: 32
<212> TYPE: PRT
<213> ORGANISM: Homo sapiens

<400> SEQUENCE: 44

Lys Arg Thr Leu Lys Ile Pro Ala Met Thr Ile Ala Lys Asn Ala Gly
1               5                   10                  15

Val Glu Gly Ser Leu Ile Val Glu Lys Ile Met Gln Ser Ser Ser Glu
                20                  25                  30

<210> SEQ ID NO 45
<211> LENGTH: 28
<212> TYPE: PRT
<213> ORGANISM: Homo sapiens

<400> SEQUENCE: 45

Lys Val Val Arg Thr Ala Leu Leu Asp Ala Ala Gly Val Ala Ser Leu
1               5                   10                  15

Leu Thr Thr Ala Glu Val Val Val Thr Glu Ile Pro
                20                  25

<210> SEQ ID NO 46
<211> LENGTH: 15
<212> TYPE: PRT
<213> ORGANISM: Homo sapiens

<400> SEQUENCE: 46

Val Ala Ser Leu Leu Thr Thr Ala Glu Val Val Val Thr Glu Ile
1               5                   10                  15

<210> SEQ ID NO 47
<211> LENGTH: 23
<212> TYPE: PRT
<213> ORGANISM: Mycobacterium

<400> SEQUENCE: 47

Thr Asp Asp Val Ala Gly Asp Gly Thr Thr Thr Ala Thr Val Leu Ala
1               5                   10                  15

Gln Ala Leu Val Arg Glu Gly
```

```
<210> SEQ ID NO 48
<211> LENGTH: 32
<212> TYPE: PRT
<213> ORGANISM: Mycobacterium

<400> SEQUENCE: 48

Asn Glu Gly Val Ile Thr Val Glu Ser Asn Thr Phe Gly Leu Gln
1               5                   10                  15

Leu Glu Leu Thr Glu Gly Met Arg Phe Asp Lys Gly Tyr Ile Ser Gly
            20                  25                  30

<210> SEQ ID NO 49
<211> LENGTH: 9
<212> TYPE: PRT
<213> ORGANISM: Mycobacterium

<400> SEQUENCE: 49

Thr Phe Gly Leu Gln Leu Glu Leu Thr
1               5

<210> SEQ ID NO 50
<211> LENGTH: 33
<212> TYPE: PRT
<213> ORGANISM: Mycobacterium

<400> SEQUENCE: 50

Arg Gln Glu Ala Val Leu Glu Asp Pro Tyr Ile Leu Leu Val Ser Ser
1               5                   10                  15

Lys Val Ser Thr Val Lys Asp Leu Leu Pro Leu Leu Glu Lys Val Ile
            20                  25                  30

Gly

<210> SEQ ID NO 51
<211> LENGTH: 15
<212> TYPE: PRT
<213> ORGANISM: Mycobacterium

<400> SEQUENCE: 51

Glu Ala Val Leu Glu Asp Pro Tyr Ile Leu Leu Val Ser Ser Lys
1               5                   10                  15

<210> SEQ ID NO 52
<211> LENGTH: 15
<212> TYPE: PRT
<213> ORGANISM: Mycobacterium

<400> SEQUENCE: 52

Pro Tyr Ile Leu Leu Val Ser Ser Lys Val Ser Thr Val Lys Asp
1               5                   10                  15

<210> SEQ ID NO 53
<211> LENGTH: 38
<212> TYPE: PRT
<213> ORGANISM: Mycobacterium

<400> SEQUENCE: 53

Lys Pro Leu Leu Ile Ile Ala Glu Asp Val Glu Gly Glu Ala Leu Ser
1               5                   10                  15

Thr Leu Val Val Asn Lys Ile Arg Gly Thr Phe Lys Ser Val Ala Val
            20                  25                  30
```

```
Lys Ala Pro Gly Phe Asp
        35

<210> SEQ ID NO 54
<211> LENGTH: 15
<212> TYPE: PRT
<213> ORGANISM: Mycobacterium

<400> SEQUENCE: 54

Gly Glu Ala Leu Ser Thr Leu Val Val Asn Lys Ile Arg Gly Thr
1               5                   10                  15

<210> SEQ ID NO 55
<211> LENGTH: 36
<212> TYPE: PRT
<213> ORGANISM: Mycobacterium

<400> SEQUENCE: 55

Thr Glu Val Glu Leu Lys Glu Arg Lys His Arg Ile Glu Asp Ala Val
1               5                   10                  15

Arg Asn Ala Lys Ala Ala Val Glu Glu Gly Ile Val Ala Gly Gly Gly
            20                  25                  30

Val Thr Leu Leu
        35

<210> SEQ ID NO 56
<211> LENGTH: 32
<212> TYPE: PRT
<213> ORGANISM: Mycobacterium

<400> SEQUENCE: 56

Lys Val Ala Leu Glu Ala Pro Leu Lys Gln Ile Ala Phe Asn Ser Gly
1               5                   10                  15

Leu Glu Pro Gly Val Val Ala Glu Lys Val Arg Asn Leu Pro Ala Gly
            20                  25                  30

<210> SEQ ID NO 57
<211> LENGTH: 33
<212> TYPE: PRT
<213> ORGANISM: Mycobacterium

<400> SEQUENCE: 57

Lys Val Thr Arg Ser Ala Leu Gln Asn Ala Ala Ser Ile Ala Gly Leu
1               5                   10                  15

Phe Leu Thr Thr Glu Ala Val Val Ala Asp Lys Pro Glu Lys Glu Lys
            20                  25                  30

Ala

<210> SEQ ID NO 58
<211> LENGTH: 15
<212> TYPE: PRT
<213> ORGANISM: Mycobacterium

<400> SEQUENCE: 58

Ile Ala Gly Leu Phe Leu Thr Thr Glu Ala Val Val Ala Asp Lys
1               5                   10                  15

<210> SEQ ID NO 59
<211> LENGTH: 15
<212> TYPE: PRT
<213> ORGANISM: Mycobacterium

<400> SEQUENCE: 59
```

-continued

```
Ile Ala Gly Leu Phe Leu Thr Thr Glu Ala Val Val Ala Asp Lys
1               5               10                  15
```

METHODS FOR EPITOPE-SPECIFIC AND CYTOKINE/ANTICYTOKINE COMBINATION IMMUNOTHERAPIES

GOVERNMENT INTERESTS

This invention was made with Government support under Grant No. AR44850, awarded by the National Institutes of Health. Accordingly, the U.S. Government may have certain rights in this invention.

FIELD OF THE INVENTION

This invention relates generally to immunotherapy methodologies in immune mediated disease states and, more specifically, to use of combination therapies to stimulate immune cells in vivo to cause modulation of pathogenic responses.

BACKGROUND OF THE INVENTION

It has long been recognized that immune inflammation comes about by a combination of antigen-specific and non-specific immune responses to a given stimulus. Antigen-specific responses comprise in part, T and B cell recognition of self and/or exogenous proteins or peptides, or even mixtures of lipids, carbohydrates and peptides, either soluble, complexed to antibodies, or processed into immunogenic peptides (i.e. epitopes) by antigen presenting cells. Recognition of an antigen leads to a response by the specific effector B or T cells and consists of a combination of cell proliferation, soluble mediator (i.e. cytokines) and/or effector (i.e. antibodies) secretion, and the expression of transmembrane proteins which govern the intensity and duration of the response through direct cell to cell contact or by soluble mediators. Under physiologic conditions, such antigen-specific responses are usually self-limited and appear to control non-specific immune mechanisms. The recognition of an antigen can also lead directly to interference with downstream events, through anergy or clonal deletion of specific cells.

Many treatment regimens have been developed for the treatment of rheumatoid arthritis and other autoimmune diseases with which immune inflammation is a complication. For example, "biologic therapies" have brought about numerous advances in the therapeutic approach to these diseases. Such therapies often include use of genetically engineered proteins. For example, monoclonal antibodies and receptor-immunoglobulin fusion proteins designed to modulate specific underlying autoimmune processes can be used and often allow for avoidance of certain problematic effects such as generalized immunosuppression. Such therapies also include use of compounds that interfere with the "trimolecular complex" that comprises the major histocompatibility complex II-Antigen-T cell receptor interactions.

Other treatment regimens are designed to block secondary signals for T cell activation and T cell interaction by using antigen-presenting cells, and cytokine agonists as well as antagonists.

Still other treatment therapies include regimens designed to affect tumor necrosis factor alpha (TNFα), which is a pivotal cytokine in the inflammatory process. For example, in one such regimen, anti-TNF reagents are used to interfere with the TNF pathway to provide short-term clinical efficacy and tolerability. Such anti-TNF reagents include infliximab which is a chimeric monoclonal anti-TNFα, soluble TNFα receptors, etanercept, and talidomide. Such therapeutic compounds also affect cytokines, for example, interleukin-1 (IL-1), wherein production of IL-1 in vivo is blocked. The blocking of IL-1 production may have beneficial effects, although the nature of such effects is still to be determined.

The use of etanercept, a fusion protein consisting of the extracellular ligand binding domain of the 75 kD receptor for TNFα and the constant portion of human IgG1, alone or in combination with methotrexate for treating patients having active rheumatoid arthritis (defined by the American College of Rheumatology (ACR) as functional class I to III) and who had previously failed to respond to treatment with greater than or equal to one disease-modifying antirheumatic drug (DMARD), produced improvements in all core ACR measures of disease activity.

Although the various above stated therapy regimens have shown a degree of success in treating autoimmune diseases, problems associated with long-term administration of such biological agents are not yet known. Both IL-1 and TNFα play important roles in normal host defenses and complications from blocking their production or effects may develop in patients. Ultimately, there is a need for careful evaluation of such therapeutics in long-term studies. There is also concern that such therapies may increase the rate of serious infections and allow for a reduced degree of control over neoplastic cells, especially in patients with severe disease. The development of antiglobulin responses to injected monoclonal antibodies and poor pharmacokinetics of low molecular-weight inhibitors are additional problems.

Other advances in treatment of autoimmune diseases include the limited use of combination-oriented therapies. For example, a treatment regimen for experimental autoimmune encephalomyelitis (EAE) has been tested using antigen-specific immunotherapy combined with cytokine therapy. In this example, local gene delivery of the interleukin-4 (IL-4) gene was administered with a tolerizing DNA vaccination; the DNA of the vaccine encoding a self-peptide proteolipid protein. This therapy demonstrated that co-delivery of two different DNAs provides protective immunity against EAE and reverse established EAE by the expression of IL-4 from the delivered naked DNA, which is secreted and acts locally on autoreactive T cells, causing the cells to shift their cytokine profile to Th 2. This treatment strategy therefore combined the antigen-specific effects of DNA vaccination and the beneficial effects of local gene delivery. However, the methodology of the treatment provided no directed control over the desired immune modulation. The ultimate efficacy of such a regimen is unknown because there is no demonstration of the capability to control the modulation of immune response.

Thus, a need exists for additional combination therapies that can more directly provide immune modulation in the treatment of immune diseases without compounding side effects. The present invention satisfies this need and provides additional advantages through a broad-based approach to immunotherapy for immune mediated diseases that allows for the controlled modulation of pathogenic immune response using a combination of epitope-specific and cytokine or anticytokine immunotherapy.

SUMMARY OF THE INVENTION

In a first embodiment, the methods of the invention provide for the combination of epitope-specific and cytokine/anticytokine therapy to achieve effective control of immune mediated disease processes. In a particularly preferred embodiment, the methods of the invention provide for a continuing regulation of immunity and control of disease manifestations through up or down regulation of innate and acquired immunity. Examples of diseases for which such methods are contemplated to be effective include, but are not limited to, rheumatoid arthritis, diabetes type I, multiple sclerosis, and inflammatory bowel disease.

In another embodiment, the methods of the invention provide for combining mechanisms for identifying and modulating epitope-specific immune responses with strategies to up or down regulate cytokine mediated responses. In another embodiment the methods of the invention lead to specific and controlled modulation of pathogenic immune responses, and eventually to control of disease in a physiologic, non-toxic and cost effective manner. Embodiments of the invention contemplate regulation of cytokine mediated responses related to inflammatory and/or tolerogenic responses associated with immunomodulatory cytokines including, but not limited to, TNFα, TNF β, IFNα, IFN β or IFN γ, IL-1, IL-4, IL-6, IL-10, IL-15 and IL-23.

In a further embodiment, the methods of the invention provide for modulating a pathogenic immune response such that the response reverts to the point in time of immune response wherein antigen-specific events are dominant and potentially relevant to disease outcome. By "dominance" of antigenic events is meant that the influence of such events is relevant enough to trigger, perpetuate or affect in any way disease pathogenesis and outcome. By "potentially relevant" is meant that the influence is theorized but not proven, and by "relevant" is meant that there is evidence to support a role in the pathogenesis. In a related embodiment, the combination of anticytokine therapy with epitope-specific therapy enables intervention of antigen-specific events to permanently and specifically induce desired antigen-specific modulation. In a particularly preferred embodiment, such modulation leads to clinically detectable amelioration of disease.

In a further related embodiment, the methods of the invention provide amelioration of disease in an antigen-specific fashion, while reducing the need for ongoing toxic, non-specific, uncontrolled, and expensive cytokine/anticytokine therapy.

In a further embodiment, the invention provides a method of modulating an immune response in a subject having an immune response-related disorder. The method includes a) administering a therapeutically effective amount of a an antigen-specific epitope, wherein administration provides epitope-specific T cell immune modulation; and b) administering a therapeutically effective amount of a cytokine or a regulatory effective amount of an agent that affects cytokine activity or expression, wherein administration of a) and b) modulates the immune response in the subject.

In another embodiment, the invention includes a method of modulating immune processes and pathogenesis of immune mediated diseases. The method includes a) identifying at least one suitable epitope; b) identifying at least one cell type associated with the immune mediated disease; and c) administering a combination of antigen-specific and cytokine or anticytokine therapy wherein the administering induces an immune response to the immune mediated disease.

In yet another embodiment, the invention provides a method of treating a subject having an immune response-related disorder. The method includes a) administering a therapeutically effective amount of a an antigen-specific epitope, wherein administration provides epitope-specific T cell immune modulation; and b) administering a therapeutically effective amount of a cytokine or a regulatory effective amount of an agent that affects cytokine activity or expression, wherein administration of a) and b) modulates the immune response in the subject, thereby treating the subject.

DETAILED DESCRIPTION OF THE INVENTION

Figure 1:
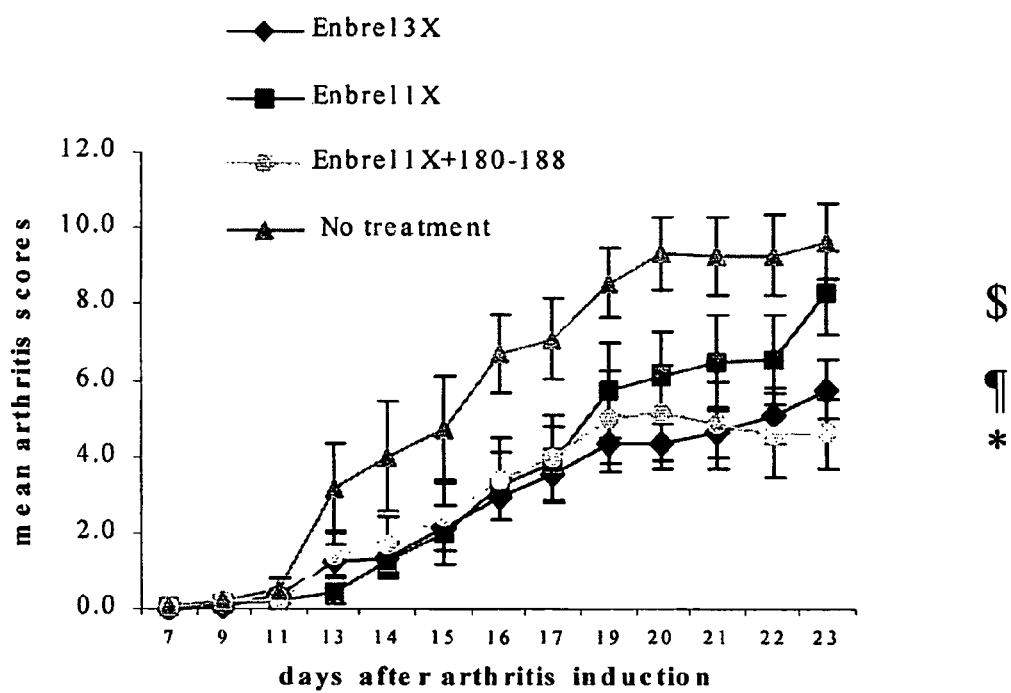
FIG. 1 is a graph showing the effects on mean arthritis scores calculated for rats divided into four groups following induction of Adjuvant Arthritis. The four treatment regimens were: (1) Etanercept alone injected 3 times; (2) Etancercept alone injected 1 time; (3) Etanercept injected 1 time with mucosal administration of mycobacterial heat shock protein 180-188; and (4) animals receiving no treatment.

The methods of the invention are directed to methods of immunotherapy that stimulate immune cells to cause modulation of pathogenic responses with limited long term effects in a non-toxic and cost effective manner. By use of the methods of the invention, pathogenic immune responses may be controlled and/or modulated. Accordingly, the autoimmune diseases from which the pathogenic response comes may also be controlled or ameliorated.

Immunotherapy is a process by which the cells of the immune system are used or stimulated in an attempt to fight disease, infection or growth. Such therapy may be passive or active. Passive immunotherapy involves direct administration of the substances (e.g., antibodies) that fight the disease. Active immunotherapy, contrarily, involves administration of the substances that stimulate the cells of the immune system to produce their own natural substances that fight the disease.

In one embodiment, the invention comprises methods wherein an immune response may be modulated by administration of a therapeutically effective amount of an antigen-specific epitope and a therapeutically effective amount of a compound that regulates the pathophysiologic role of a cytokine.

The administration of the compounds in the methods of the invention may be performed by any of the methods known to those of skill in the art. Such methods include, but are not limited to, direct administration by mucosal, intravenous (iv), subcutaneous (sc), or intramuscular (im) administration.

The invention methods include identification of proteins from T cell epitopes, where the proteins are targets of T cell immune responses. By "T cell epitope(s)" is meant a contiguous amino acid sequence recognized by a T cell in the context of the restricting MHC molecule. In one embodiment, the invention methods comprise a combination of epitope composition prediction within a protein by computer programming and actual epitope mapping methods. These computer programs and mapping techniques are well understood by those of skill in the art. In a related embodiment, epitope-specific T cells are characterized phenotypically and functionally. By "phenotypically" is meant a phenotypic characterization that identifies membrane proteins. By "functionally" is meant a characterization that identifies cell responses related to antigens e.g., cell proliferation and production of inter- and intracellular mediators. Such characteristics are then correlated with clinical variables, including disease activity and gravity. Epitopes that are relevant to a given pathogenic pathway are thereby identified.

Epitopes found to be relevant to a given pathogenic pathway are also therefore related to either up- or down-regulation of inflammation in any particular disease state for which epitopes are sought. Down-regulation is desirable in those morbid conditions, such as autoimmunity, in which control of self reactivity may lead to clinical improvement. Up-regulation is desirable in those diseases in which generation of inflammation may lead to improved defenses. Examples of such diseases include, but are not limited to, infection caused by foreign biological and chemical agents and cancer.

In one embodiment of the invention, epitopes, or epitope-specific T cells, are identified and characterized by, but not limited to:

i) Computerized analysis of putative epitopes on immunologically relevant proteins (e.g., see U.S. Pat. No. 6,037,135.);

ii) Evaluation of antigenicity in animal models in vivo and in vitro and in human diseases in vitro or ex vivo by means known to those skilled in the art;

iii) Identification and isolation of epitope-specific T cells from patients' samples by fluororochrome tagged artificial antigen presenting cells (such as described in PCT/US99/24666); and iv) Characterization of isolated epitope-specific T cells by means known to those skilled in the art.

Specific examples of antigen-specific epitopes further include epitopes in any of the following peptides in Table 1. These peptides include, but are not limited to, derivatives or mutants/analogs of heat shock 60 (HSP60) proteins and dnaJ proteins of human and prokaryotic, (i.e., mycobacteria or *E. coli*) origin.

Table 1

| Origin | Protein | Position | Sequence |
|---|---|---|---|
| *E. coli* | dnaJp2 | | VLTDSQKRAAYDQYG (SEQ ID NO: 1) |
| *E. coli* | dnaJ 4 | | QDYYEILGVSKTAEE (SEQ ID NO: 2) |
| *E. coli* | dnaJ 22 | | RKAYKRLAMKYHPDR (SEQ ID NO: 3) |
| *E. coli* | dnaJ 61 | | QKRAAYDQYGHAAFEQ (SEQ ID NO: 4) |
| *E. coli* | dnaJ 174 | | QGFFAVQQTCPHCQG (SEQ ID NO: 5) |
| *E. coli* | dnaJ 209 | | SKTLSVKIPGAVDTG (SEQ ID NO: 6) |
| *E. coli* | dnaJ 242 | | GDLYVQVQVKQHPIF (SEQ ID NO: 7) |
| *E. coli* | dnaJ 264 | | YCEVPINFAMAALGG (SEQ ID NO: 8) |
| *E. coli* | dnaJ 268 | | PINFAMAALGGEIEV (SEQ ID NO: 9) |
| *E. coli* | DnaJp1 | | QKRAAYDQYGHAAFE (SEQ ID NO: 10) |
| *E. coli* mutant | dnaJpV | | DERAAYDQYGHAAFE (SEQ ID NO: 11) |
| *E. coli* | HSP60 | 212-226 | AVELESPFILLADKK (SEQ ID NO: 12) |
| *E. coli* | HSP60 | 218-232 | PFILLADKKISNIRE (SEQ ID NO: 13) |
| *E. coli* | HSP60 | 256-270 | GEALATLVVNTMRGI (SEQ ID NO: 14) |
| *E. coli* | HSP60 | 510-524 | VAGLMITTECMVTDL (SEQ ID NO: 15) |
| human | S1 HLA | | QKRAAVDTYCRHNYG (SEQ ID NO: 16) |
| human | S2 HLA | | KDLLEQKRAAVDTYC (SEQ ID NO: 17) |
| human | 2 (HSJI) | | ASYYEILDVPRSASA (SEQ ID NO: 18) |
| human | 3 (HDJ1) | | KDYYQTLGLARGASD (SEQ ID NO: 19) |
| human | 5 (HDJ2) | | TTYYDVLGVKPNATQ (SEQ ID NO: 20) |
| human | 20 (HSJ1) | | KKAYRRKALQWHPDK (SEQ ID NO: 21) |
| human | 21 (HDJ1) | | KRAYRRQALRYHPDK (SEQ ID NO: 22) |
| human | 23 (HDJ2) | | KKAYRKLALKYHPDK (SEQ ID NO: 23) |
| human | 164 (HSJ1) | | FRSVSTSTTFVQGRR (SEQ ID NO: 24) |

Table 1-continued

| Origin | Protein | Position | Sequence |
|---|---|---|---|
| human | 167 (HDJ2) | | PGMVQQIQSVCMECQ (SEQ ID NO: 25) |
| human | 176 (HSJ1) | | GRRITTRRIMENGQE (SEQ ID NO: 26) |
| human | 50 (HDJ2) | | QAYEVLSDAKKRELYD (SEQ ID NO: 27) |
| human | 51 (HSJ1) | | EAYEVLSDKHKREIYD (SEQ ID NO: 28) |
| human | 134 (HSJ1) | | SGPFFTFSSSFPGHS (SEQ ID NO: 29) |
| human | 197 (HSJ1) | | DGQLKSVTINGVPDD (SEQ ID NO: 30) |
| human | 254 (HSJ1) | | DLQLAMAYSLSEMEA (SEQ ID NO: 31) |
| human | 256 (HDJ2) | | EDLFMCMDIQLVEAL (SEQ ID NO: 32) |
| human | 270 (HDJ2) | | LCGFQKPISTLDNRT (SEQ ID NO: 33) |
| human | 283 (HDJ2) | | RTIVITSHPGQIVKH (SEQ ID NO: 34) |
| human | 318 (HDJ2) | | GRLIIEFKVNFPENG (SEQ ID NO: 35) |
| human | HSP60 | 105-127 | TNEEAGDGTTTATVLARSIAKEG (SEQ ID NO: 36) |
| human | HSP60 | 195-226 | RKGVITVKDGKTLNDELEIIEGMKFDRGYISP (SEQ ID NO: 37) |
| human | HSP60 | 234-266 | GQKCEFQDAYVLLSEKKISSIQSIVPALEIANA (SEQ ID NO: 38) |
| human | HSP60 | 236-250 | KCEFQDAYVLLSEKK (SEQ ID NO: 39) |
| human | HSP60 | 242-256 | AYVLLSEKKISSIQS (SEQ ID NO: 40) |
| human | HSP60 | 269-307 | KPLVIIAEDVDGEALSTLVLNRLKVGLQVVAVKAPGFGD (SEQ ID NO: 41) |
| human | HSP60 | 280-294 | GEALSTVLVLNRLKVG (SEQ ID NO: 42) |
| human | HSP60 | 410-445 | SDVEVNEKKDRVTDALNATRAAVEEGIVLGGGCALL (SEQ ID NO: 43) |
| human | HSP60 | 469-502 | KRTLKIPAMTIAKNAGVEGSLIVEKLMQSSSE (SEQ ID NO: 44) |
| human | HSP60 | 523-656 | KVVRTALLDAAGVASLLTTAEVVVTEIP (SEQ ID NO: 45) |
| human | HSP60 | 535-549 | VASLLTTAEVVVTEI (SEQ ID NO: 46) |
| mycobacterium | HSP60 | 80-102 | TDDVAGDGTTTATVLAQALVREG (SEQ ID NO: 47) |
| mycobacterium | HSP60 | 169-200 | NEGVITVEESNTFGLQLELTEGMRFDKGYISG (SEQ ID NO: 48) |
| mycobacterium | HSP60 | 180-188 | TFGLQLELT (SEQ ID NO: 49) |
| mycobacterium | HSP60 | 208-240 | RQEAVLEDPYILLVSSKVSTVKDLLPLLEKVIG (SEQ ID NO: 50) |
| mycobacterium | HSP60 | 210-224 | EAVLEDPYILLVSSK (SEQ ID NO: 51) |
| mycobacterium | HSP60 | 216-230 | PYILLVSSKVSTVKD (SEQ ID NO: 52) |
| mycobacterium | HSP60 | 243-281 | KPLLIIAEDVEGEALSTLVVNKIRGTFKSVAVKAPGFD (SEQ ID NO: 53) |
| mycobacterium | HSP60 | 254-268 | GEALSTLVVNKIRGT (SEQ ID NO: 54) |
| mycobacterium | HSP60 | 383-418 | TEVELKERKHRIEDAVRNAKAAVEEGIVAGGGVTLL (SEQ ID NO: 55) |
| mycobacterium | HSP60 | 441-478 | KVALEAPLKQIAFNSGLEPGVVAEKVRNLPAG (SEQ ID NO: 56) |

Table 1-continued

| Origin | Protein | Position | Sequence |
|---|---|---|---|
| mycobacterium | HSP60 | 494-527 | KVTRSALQNAASIAGLFLTTEAVVADKPEKEKA (SEQ ID NO: 57) |
| mycobacterium | HSP60 | 503-517 | IAGLFLTTEAVVADK (SEQ ID NO: 58) |
| mycobacterium | HSP60 | 507-521 | IAGLFLTTEAVVADK (SEQ ID NO: 59) |

In still another embodiment, immunotherapy is carried out in at least two distinct phases comprising "induction" and "consolidation" therapy periods.

By "induction period" is meant a period of time used for down-regulation of non-specific inflammation to allow for generation of regulatory epitope-specific T cell responses. In this time period, a subject patient is treated with a combined administration of compounds that up- or down-regulate cytokines important in a particular disease state of interest with antigen-specific immune modulation. The objective of this treatment period is to create an appropriate environment for antigen-specific T cell regulation.

The immunological environment to be generated depends on whether there is a need for up- or down-regulation. For example, for those cases requiring down-regulation of inflammation (e.g., autoimmunity), blocking, inhibiting or destruction of one or more pro-inflammatory or activating cytokines is carried out. Conversely, when up-regulation of antigen-specific T cell responses is desired immunostimulatory cytokines are employed to boost defensive immune responses. Up-regulation may be desired, for example, in infectious disease treatments, vaccinations and cancer regimens. Immunomodulatory cytokines that can be used in the above stated up or down regulation, depending upon the desired outcome include, but are not limited to IFNα, IFNβ, IFNγ, TNFα, TNFβ, TGFβ, IL-2, IL-4, IL-6, IL-10, IL-12, IL-15 and IL-23.

As used herein the term "cytokine" encompasses chemokines, interleukins, lymphokines, monokines, colony stimulating factors, and receptor associated proteins, and functional fragments thereof. As used herein, the term "functional fragment" refers to a polypeptide which possesses biological function or activity that is identified through a defined functional assay.

The cytokines, colony stimulating factors (CSF), and interleukins (IL) useful as a proteinaceous ligand moiety include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, and the like, which bind, respectively, to the EMAP-II, GM-CSF, G-CSF, M-CSF, IL-1, IL-2, IL-3, IL-4, IL-5, IL-6, IL-12, IL-13 families of cytokine receptors, and the like, and which is associated with a particular biologic, morphologic, or phenotypic alteration in a cell or cell mechanism.

Soluble receptors of cytokines may also be utilized in the methods of the invention by acting as anti-cytokines in that they can be administered to compete with the natural target of the cytokines. Examples of soluble receptors applicable to the current invention include, but are not limited to, soluble receptors specific for IL-1 and TNFα. The production of such soluble receptors and their respective use are well known to those of skill in the art.

Cytokine antagonists can take several forms. They may be monoclonal antibodies. They may be a monoclonal antibody fragment. They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. Thus, a cytokine antagonist of the invention also includes soluble receptors or fragments thereof. An even more potent antagonist consists of two soluble receptors fused together to a specific portion of an immunoglobulin molecule (Fc fragment). This produces a dimer composed of two soluble receptors which have a high affinity for the target, and a prolonged half-life. This new molecule is called a fusion protein. An example of this new type of molecule, called a fusion protein, is etanercept (Enbrel®.).

TNF, a naturally occurring cytokine, plays a key role in the inflammatory response, in the immune response, and in the response to infection. TNF is formed by the cleavage of a precursor transmembrane protein, forming soluble molecules which aggregate in vivo to form trimolecular complexes. These complexes then bind to receptors found on a variety of cells. Binding produces an array of effects, including release of other immunomodulatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Interleukin-1 (IL-1) is a cytokine which has been implicated in the inflammatory response occurring in the brain, spinal cord, retina, muscle, and elsewhere in the body. There are two naturally occurring inhibitors of IL-1 in the body: IL-1 receptor antagonist (IL-1 RA) and IL-1 receptor type II (IL-1 R type II). Additional inhibitors of IL-1 for the purpose of this patent are soluble IL-1 receptors: fusion proteins consisting of two IL-1 receptors attached to the Fc portion of a human IgG molecule (IL-1 R-FP); and monoclonal antibodies with a high affinity for IL-1. IL-6 and IL-8 are both also immunomodulatory cytokines.

Agents useful for administration to a subject for regulating cytokine activity or expression or a cytokine receptor also include antibodies or fragments thereof, a peptide, a peptidomimetic, a polynucleotide, a small organic molecule, or any other agent, that can act directly or indirectly as an agonist of cytokine signal transduction or as an antagonist of cytokine signal transduction. In another embodiment, the agent can specifically interact with a cytokine or cytokine receptor expressed by a cell. For example, a peptide agent is exemplified by an anti-cytokine or cytokine receptor antibody or by an anti-idiotypic antibody of an anti-cytokine or cytokine antibody. Such a peptide agent provides the additional advantage that it can be selected not only for its ability to interact specifically with a cytokine or cytokine receptor, thereby competing with cytokine or cytokine for the receptor, but can be further selected to have an ability to not activate cytokine signal transduction for example.

As used herein, the term "antibody" is used in its broadest sense to include polyclonal and monoclonal antibodies, as well as antigen binding fragments of such antibodies. An antibody useful in a method of the invention, or an antigen binding fragment thereof, is characterized, for example, by having specific binding activity for an epitope. In addition, as discussed above, an antibody of the invention can be an antibody that specifically binds a peptide portion of a polypeptide.

The term "binds specifically" or "specific binding activity," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity for an epitope, are included within the definition of an antibody. For purposes of the present invention, an antibody may specifically react with an epitope of a cytokine or cytokine receptor, for example, is considered to not substantially cross react with another cytokine or cytokine receptor if the antibody has at least a two-fold greater binding affinity, generally at least a five-fold greater binding affinity, and particularly at least a ten-fold greater binding affinity for the cytokine or cytokine receptor as compared to the related cytokine or cytokine receptor.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., Science 246:1275-1281 (1989).). These and other methods of making, for example, chimeric, humanized, CDR-grafted, single chain, and bifunctional antibodies are well known to those skilled in the art (Winter and Harris, Immunol. Today 14:243-246, 1993; Ward et al., Nature 341:544-546, 1989; Harlow and Lane, Antibodies: A laboratory manual (Cold Spring Harbor Laboratory Press, 1988); Hilyard et al., Protein Engineering: A practical approach (IRL Press 1992); Borrabeck, Antibody Engineering, 2d ed. (Oxford University Press 1995).).

If desired, a kit incorporating an antibody or other agent useful in a method of the invention can be prepared. Such a kit can contain, in addition to the agent, a pharmaceutical composition in which the agent can be reconstituted for administration to a subject. The kit also can contain, for example, reagents for detecting the antibody, or for detecting specific binding of the antibody to a cytokine or cytokine receptor. Such detectable reagents useful for labeling or otherwise identifying the antibody are described herein and known in the art.

Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol.* (1992), section 2.4.1.). In addition, monoclonal antibodies can be obtained using methods that are well known and routine in the art (Harlow and Lane, supra, 1988). For example, spleen cells from a mouse immunized with a cytokine or cytokine receptor, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated and utilized as a continuous source of the antibodies. The antibodies can be further screened for the inability to bind specifically with the cytokine or cytokine receptor. Such antibodies are useful, for example, for preparing standardized kits for clinical use. A recombinant phage that expresses, for example, a single chain anti-cytokine or cytokine receptor antibody also provides an antibody that can used for preparing standardized kits.

Methods of preparing monoclonal antibodies well known (see, for example, Kohler and Milstein, Nature 256:495, 1975; see, also, Coligan et al., supra, 1992, see sections 2.5.1-2.6.7; Harlow and Lane, supra, 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures.

Monoclonal antibodies can be isolated and purified from hybridoma cultures by a variety of well established techniques, including, for example, affinity chromatography with Protein-A SEPHAROSE, size exclusion chromatography, and ion exchange chromatography (Coligan et al., supra, 1992, see sections 2.7.1-2.7.12 and sections 2.9.1-2.9.3; see, also, Barnes et al., "Purification of Immunoglobulin G (IgG)," in *Meth.: Molec. Biol.* 10:79-104 (Humana Press 1992).). Methods of in vitro and in vivo multiplication of monoclonal antibodies is well known to those skilled in the art. Multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention can also be derived from subhuman primate antibody. General techniques for raising therapeutically useful antibodies in baboons can be found, for example, in Goldenberg et al., International Patent Publication WO 91/11465 (1991); and Losman et al., *Int. J. Cancer* 46:310, 1990.

A therapeutically useful anti-cytokine or cytokine receptor antibody also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are known (see, for example, Orlandi et al., *Proc. Natl. Acad. Sci., USA* 86:3833, 1989.). Techniques for producing humanized monoclonal antibodies also are known (see, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci., USA* 89:4285, 1992; Sandhu, *Crit. Rev. Biotechnol.* 12:437, 1992; and Singer et al., *J. Immunol.* 150:2844, 1993.).

Antibodies of the invention also can be derived from human antibody fragments isolated from a combinatorial immunoglobulin library (see, for example, Barbas et al., *METHODS: A Companion to Methods in Immunology* 2:119, 1991; Winter et al., *Ann. Rev. Immunol.* 12:433, 1994.). Cloning and expression vectors that are useful for producing a human immunoglobulin phage library can be obtained, for example, from STRATAGENE Cloning Systems (La Jolla, Calif.).

An antibody of the invention also can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immunol.* 6:579, 1994.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. No. 4,036,945 and U.S. Pat. No. 4,331,647; and references contained therein; Nisonhoff et al., *Arch. Biochem. Biophys.* 89:230. 1960; Porter, *Biochem. J.* 73:119, 1959; Edelman et al., *Meth. Enzymol,* 1:422 (Academic Press 1967); see, also, Coligan et al., supra, 1992, see sections 2.8.1-2.8.10 and 2.10.1-2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of $V_H$ and $V_L$ chains. This association can be noncovalent (Inbar et al., *Proc. Natl. Acad. Sci., USA* 69:2659, 1972). Alternatively, the variable chains can be linked by an intermolecular disulfide bond or cross-linked by chemicals such as glutaraldehyde (Sandhu, supra, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2:97, 1991; Bird et al., *Science* 242:423-426, 1988; Ladner et al., U.S. Pat. No. 4,946,778; Pack et al., *Bio/Technology* 11: 1271-1277, 1993; see, also Sandhu, supra, 1992.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991.).

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent application, the terms blocker, inhibitor, and antagonist are used interchangeably with respect to cytokines.

Advances in biotechnology have resulted in improved molecules as compared to simply using monoclonal antibodies. One such molecule is an antibody fragment. By removing part of the antibody structure, the function of this molecule is changed so that it acts differently in the human body. Another new type of molecule, distinct from monoclonal antibodies and soluble receptors, is a fusion protein. Such molecules have a distinct function which acts differently in the human body than a simple soluble receptor or receptors.

An agent useful in a method of the invention also can be a polynucleotide. Generally, but not necessarily, the polynucleotide is introduced into the cell, where it effects its function either directly, or following transcription or translation or both. For example, the polynucleotide agent can encode a peptide, which is expressed in the cell and modulates a cytokine or cytokine receptor activity. Such an expressed peptide can be, for example, a mutant cytokine or cytokine receptor such as a soluble cytokine or cytokine receptor extracellular domain; a cytokine or cytokine receptor extracellular domain operatively associated with a membrane anchoring domain; or a mutant cytokine or cytokine receptor lacking activity.

A polynucleotide of the invention, including a polynucleotide agent useful in performing a method of the invention, can be contacted directly with a target cell. For example, oligonucleotides useful as antisense molecules, ribozymes, or triplexing agents can be directly contacted with a target cell, whereupon the enter the cell and effect their function. A polynucleotide agent also can interact specifically with a polypeptide, for example, a receptor (or the cytokine itself), thereby altering the ability of a cytokine to interact specifically with the receptor. Such polynucleotides, as well as methods of making and identifying such polynucleotides, are disclosed herein or otherwise well known in the art (see, for example, O'Connell et al., Proc. Natl. Acad. Sci., USA 93:5883-5887, 1996; Tuerk and Gold, Science 249:505-510, 1990; Gold et al., Ann. Rev. Biochem. 64:763-797, 1995.).

An expression vector can contain the expression elements necessary to achieve, for example, sustained transcription of the encoding polynucleotide, or the regulatory elements can be operatively linked to the polynucleotide prior to its being cloned into the vector. An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzymol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993.).

Mechanisms of administration of cytokine/anticytokine therapy of the invention include, but are not limited to: i) direct administration of cytokines by mucosal, intravenous (iv), subcutaneous (sc), or intramusculatory (im) routes; ii) injection of DNA constructs encoding one or more cytokines; iii) conditioning ex vivo of relevant cell subtypes (e.g., T or B cells) by soluble cytokines in the same microenvironment; iv) administration of antibodies (e.g., human, non-human, and/or chimeric) designed to bind soluble or membrane bound cytokine receptors; v) administration of antibodies (e.g., human, non-human, and/or chimeric) designed to bind soluble or membrane bound cytokines; and vi) soluble cytokine receptors, engineered to interfere with the physiological targets of naturally released cytokines. Additional treatments are known to those of skill in the art.

Induction of epitope-specific therapy according to the present invention provides for initial identification of suitable epitopes, as described above, and subsequent generation, in vivo and/or ex vivo, of T cells capable of modulating immune responses. Examples of approaches for epitope-specific therapy include various approaches to induce modulation, in vivo and ex vivo, of epitope-specific responses including, but not limited to:

i) tolerization to an immunomodulatory peptide via mucosal (i.e. nasal or oral) tolerization;

ii) boosting of epitope-specific immune responses via sc, iv or im immunizations with proteins and epitopes or DNA encoding such proteins or epitopes;

iii) regulation of epitope-specific responses by expansion in vivo and ex vivo of epitope-specific-regulatory T cells; and iv) modulation ex vivo of epitope-specific T cells by means of artificial antigen presenting cells with or without conditioning environment. By "conditioning environment" is meant a microenvironment in which T cell responses may be modulated by adding to the medium soluble mediators (e.g., cytokines), and/or by soluble or support bound molecules (e.g., co-stimulatory molecules) capable of inducing a given T cell response.

In the invention methods, the induction period lasts for the time necessary for both treatments as described above to act, the induction period comprising the time for the cytokine/anticytokine oriented treatment to change the immune environment as desired via either up or down regulation, and for the epitope-specific T cells to be expanded. Generally, this period requires between one and three months, preferably two months in humans. This period may vary in accordance with the individual treatment.

Effective induction of epitope-specific T cells is preferably monitored by means of monitoring T cell modulation e.g. by a mechanism described in PCT/US99/24666 by T cell capture. Such monitoring may also be accomplished by other means known to those skilled in the art.

Following demonstration that regulatory T cells of a desired specificity of interest have been generated by the above described generation of epitope-specific responses (i.e., a T cell population with functional and phenotypical characteristics capable of modulating the immune response), the consolidation period is performed. Mechanisms for monitoring the generation and characteristics of T cell populations comprise, but are not limited to: i) T cell capture by means of fluorochrome tagged artificial antigen presenting cells; ii) Tetramer technology; iii) dimer technology; and iv) monitoring of CD69+ cells by flow cytometry. By "T cell capture" is meant identification, isolation and manipulation of antigen-specific cells by means of artificial antigen presenting cells, as described in PCT/US99/24666. By "tetramer technology" is meant a recombinant multiple (4×) of MHC/peptide complexes used to identify cells of a desired specificity. By "dimers technology" is meant a recombinant multiple (2×) of MHC/peptide complexes used to identify cells of a desired specificity (see for example, U.S. Pat. No. 5,635,363.).

The epitope-specific peptides may be prepared in a variety of ways. Conveniently, they can be synthesized by conventional techniques employing automatic synthesizers, or may be synthesized manually. Alternatively, DNA sequences can be prepared which encode the particular peptide and may be cloned and expressed to provide the desired peptide. In this instance a methionine may be the first amino acid. In addition, peptides may be produced by recombinant methods as a fusion to proteins that are one of a specific binding pair, allowing purification of the fusion protein by means of affinity reagents, followed by proteolytic cleavage, usually at an engineered site to yield the desired peptide (see for example Driscoll et al. (1993) J. Mol. Bio. 232:342-350). The peptides may also be isolated from natural sources and purified by known techniques, including, for example, chromatography on ion exchange materials, separation by size, immunoaffinity chromatography and electrophoresis. Of particular interest in the present invention, peptides derived from hsp60 and dnaJ from any of human, mycobacteria and *E. coli* are useful.

During the consolidation period, the cytokine/anticytokine treatment is suspended or dramatically reduced, while the epitope-specific immunotherapy is continued. Hence, the benefits of a non-toxic and well focused and controlled consolidated approach is provided, while the undesirable effects of the non-specific cytokine/anticytokine treatment is eliminated or reduced. As provided below in Example 1, this approach is shown to be effective as prolonged anticytokine therapy in inducing and maintaining a controllable immunotherapy-directed remission in autoimmune disease, while allowing complete withdrawal from the anticytokine treatment after the induction phase.

Application of this combination treatment regimen is valuable in numerous disease states that are sensitive to immune modulation. Up or down regulation of any number of cytokines and chemokines may be manipulated. For example not only can IL-10 and TGFβ be regulated in a controlled manner, as set forth in Example 1 below, but also other cytokines disclosed herein.

The two part treatment regimen provides identification of epitopes specific for a disease of interest rather than traditional methods that apply non-specific approaches. This identification of epitope is combined with specific immune modulation of a host's pathophysiology that is directly related to the particular disease. By such peptide-specific therapy, a change in the absolute numbers of peptide-specific T cells can be determined as well as quality of the T cell's response as they are involved in the pathology process. Example 1, set forth below, wherein the approach is applied using heat shock peptide 180-188, demonstrates that this method is applicable to peptide epitopes such as those derived from heat shock proteins. Specifically, a tailored/controlled immune modulation can be engineered using an immune therapy regimen that provides substantial benefit when combined with modulation of a host's pathophysiology. This novel controllable approach ultimately results in a significant reduction in the use of "traditional" therapeutic agents being administered to patients providing both an economic and clinical benefit.

One skilled in the art would readily appreciate that the present invention is well adapted for use in immunotherapy for modulation of pathogenic immune responses in immune mediated diseases.

The present invention provides a method of ameliorating a disorder such as an arthritis in a subject, wherein the epitope-specific immune responses have been identified. Such disorders may include, but are not limited to: rheumatoid arthritis and osteoarthritis.

As used herein, the term "ameliorate" means that signs or symptoms associated with an identified disorder are lessened. The signs or symptoms to be monitored will be characteristic of the particular disorder and will be well known to skilled clinician, as will the methods for monitoring the signs and conditions. For example, where the disorder is rheumatoid arthritis, the clinician will know that increased joint mobility or dexterity exhibited by the subject; or decreased inflammatory response as evidenced by lower cytokine levels or fewer inflammatory cells; or reduced level or decreased rate of joint and/or cartilage destruction as evidenced by an imaging method, are indicative of a method of the invention ameliorating the arthritis. Similarly, where the disorder is osteoarthritis, the clinician will know that a decrease in joint and/or cartilage damage is indicative of ameliorating the arthritis. focused and controlled consolidated approach is provided, while the undesirable effects of the non-specific cytokine/anticytokine treatment is eliminated or reduced. As provided below in the examples, this approach is shown to be effective as prolonged anticytokine therapy in inducing and maintaining a controllable immunotherapy-directed remission in autoimmune disease, while allowing complete withdrawal from the anticytokine treatment after the induction phase.

Detection of T cell specific epitopes is of interest in connection with a variety of conditions associated with T cell activation. Such conditions include autoimmune diseases, e.g. multiple sclerosis, myasthenia gravis, rheumatoid arthritis, type 1 diabetes, graft vs. host disease, Grave's disease, etc.; various forms of cancer, e.g. carcinomas, melanomas, sarcomas, lymphomas and leukemias. Various infectious diseases such as those caused by viruses, e.g. HIV-1, hepatitis, herpes viruses, enteric viruses, respiratory viruses, rhabdovirus, rubeola, poxvirus, paramyxovirus, morbillivirus, etc. are of interest. Infectious agents of interest also include bacteria, such as *Pneumococcus, Staphylococcus, Bacillus. Streptococcus, Meningococcus, Gonococcus, Eschericia, Klebsiella, Proteus, Pseudomonas, Salmonella, Shigella, Hemophilus, Yersinia, Listeria, Corynebacterium, Vibrio, Clostridia, Chlamydia, Mycobacterium, Helicobacter* and *Treponema*; protozoan pathogens, and the like. T cell associated allergic responses may also be monitored, e.g. delayed type hypersensitivity or contact hypersensitivity involving T cells.

Of particular interest are conditions having an association with a specific peptide or MHC haplotype, where the subject binding complexes may be used to track the T cell response with respect to the haplotype and antigen. A large number of associations have been made in disease states that suggest that specific MHC haplotypes, or specific protein antigens are responsible for disease states. However, direct detection of reactive T cells in patient samples has not been possible. Detection and quantitation with the subject binding complexes allows such direct detection. As examples, the activity of cytolytic T cells against HIV infected CD4+ T cells may be determined with the subject methods. The association of diabetes with the DQB1*0302 (DQ3.2) allele may be investigated by the detection and quantitation of T cells that recognize this MHC protein in combination with various peptides of interest. The presence of T cells specific for peptides of myelin basic protein in conjunction with MHC proteins of multiple sclerosis patients may be determined. The antigenic specificity may be determined for the large number of activated T cells that are found in the synovial fluid of rheumatoid arthritis patients. It will be appreciated that the subject methods are applicable to a number of diseases and immune-associated conditions.

The isolation of antigen specific T cells finds a wide variety of applications. The isolated T cells may find use in the treatment of cancer as in the case of tumor-infiltrating lymphocytes. Specific T cells may be isolated from a patient, expanded in culture by cytokines, antigen stimulation, etc., and replaced in the autologous host, so as to provide increased immunity against the target antigen. A patient sample may be depleted of cells reactive with a specific antigen, to lessen an autoimmune response.

Inhibition of immune function may be achieved by inducing anergy of specific T cells, or by ablation of reactive T cells. The subject binding complexes allow a therapy to be targeted to very specific subsets of T cells. The ability to inhibit immune system functions is known to be therapeutically useful in treating a variety of diseases such as atherosclerosis, allergies, autoimmune diseases, certain malignancies, arthritis, inflammatory bowel diseases, transplant rejection and reperfusion injury. Specific diseases of interest include systemic lupus erythematosus; rheumatoid arthritis; polyarteritis nodosa; polymyositis and dermatomyositis progressive systemic sclerosis (diffuse scleroderma); glomerulonephritis; myasthenia gravis; Sjogren's syndrome; Hashimoto's disease; Graves' disease; adrenalitis; hypoparathyroidism; pernicious anemia; diabetes; multiple sclerosis, and related demyelinating diseases; uveitis; pemphigus and pemphigoid cirrhosis; ulcerative colitis; myocarditis; regional enteritis; adult respiratory distress syndrome; local manifestations of drug reactions, such as dermatitis, etc.; inflammation-associated or allergic reaction patterns of the skin; atopic dermatitis and infantile eczema; contact dermatitis; psoriasis; lichen planus; allergic enteropathies; allergic rhinitis; bronchial asthma; transplant rejection, e.g. heart, kidney, lung, liver, pancreatic islet cell, etc.; hypersensitivity or destructive responses to infectious agents; poststreptococcal diseases, e.g. cardiac manifestations of rheumatic fever, and the like.

In addition to the combination immunotherapy described here, it may be desirable to also ablate specific T cells, the subject binding complexes may be conjugated to a toxin moiety. Various cytotoxic agents are known and have been used in conjunction with specific binding molecules. Illustrative of these compounds are ricin, abrin, diphtheria toxin, maytansinoids, cisplatin, and the like. Where there are two subunits, only the cytotoxic subunit may be used, e.g. the .alpha.-unit of ricin. The toxin is conjugated to the binding complex, generally by means of a cross-linker, or other conjugation that includes a disulfide bond. Toxin conjugates are disclosed in U.S. Pat. Nos. 5,208,020; 4,863,726; 4,916,213; and 5,165,923. The toxin conjugate is administered so as to specifically eliminate the target T cells without exerting significant toxicity against other cells.

The subject binding complexes may be administered to a host to induce anergy of the specific T cells. The binding complex will induce T cell anergy upon binding, because the co-stimulator molecules necessary for T cell activation are not present. The binding complexes are administered to individuals, preferably mammals, in a manner that will maximize the likelihood of the binding complexes reaching the targeted T cell and binding to it, and thereby inducing anergy. This in turn will inhibit the immune response mediated by that T cell.

The following examples are intended to illustrate but not limit the invention.

EXAMPLE 1

In this example, a comparison is made between currently used traditional treatment methods and the invention methods. Performance of traditional methods of treating humans to lower the inflammatory processes arising due to TNFα includes administration of etanercept, (commercially known as Enbrel Æ (Immunex, Seattle, Wash.) a soluble recombinant TNFα receptor/IgG1 molecule that is administered to reduce the presence of TNFα. This example provides data using a rat model (which is recognized as directly correlating with human response) showing that the combination therapy method of the invention provides substantial reduction of side effects with clinically significant benefits and reduction of the need to administer etanercept. (Typically, the use of etanercept in patients is not only very expensive, but also has unforeseen long term side effects, presents an increased risk for opportunistic infection and malignancy, and relapse of disease will occur if administration is stopped.)

In the animal model of this Example, such immunomodulatory treatment was used in combination with induction of mucosal tolerance. The clinical outcome was then monitored and immunological characterization of T cells was performed. Adjuvant Arthritis was induced by injection into the base of the subject rat tail of 0.1 mg of etanercept (Day 0). At Day 8, daily arthritis scores (having a maximum reading of 16) were measured and the rats were weighed every other day. Treqatment was begun at Day 9.

Subject rats were divided into four treatment groups: etanercept 3×sc at day 9, 11, 13; etanercept 1×sc at day 9; etanercept 1×sc at Day 9 and heat shock peptide 180-188 administered on days 10, 13, 16, and 19; and no treatment group. Etanercept was dosed at 0.3 mg/kg of body weight. Heat shock peptide 180-188 was dosed at 100 ug. (The heat shock peptide was that of mycobacterial protein 180-188 and known to be the main epitope recognized by T cells that are pathogenic in adjuvant arthritis).

Results of the above stated administration are shown in FIG. 1. As is clear from the graph, combined treatment regimen comprising one injection of etanercept with multiple exposure of heat shock peptide to mucosa reduced the arthritis score. Additionally, mandibular and inguinal lymph nodes were harvested from the subject rats at days 22-35 and the cells were cultured in vitro, in order to confirm the theory that the underlying mechanism for the positive efficacy of the combination treatment regimen includes a functional switch from a Th1 to a Th2 response. Proliferation of the cells was carried out by [3H] TdR incorporation. Intracellular cytokine production and surface marker expression was tested using FACS. Cytokine and Tbet and GATA-3 gene transcription were carried out by Taqman.

Figure 2:
FIG. 2 is as set of graphs showing the stimulation of mandibular lymph node cells for each of the four test groups shown in FIG. 1. The bars labeled 180-188, Mt, and OVA represent that the culture conditions used these as antigens in the media for accessing the stimulation index.
Figure 2:
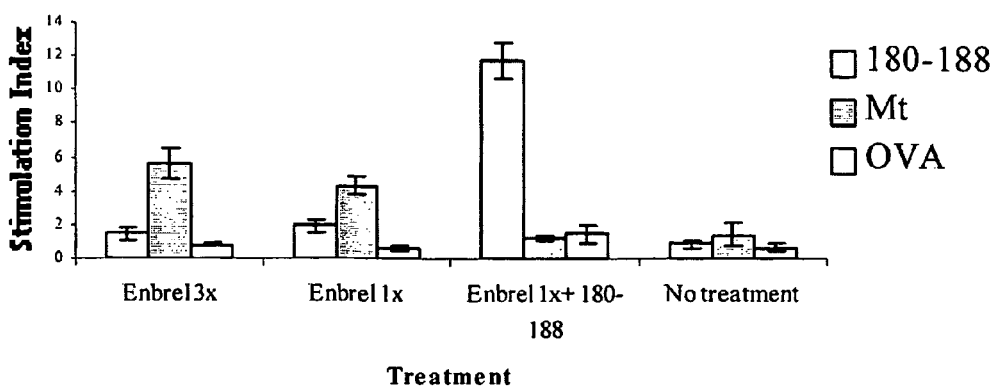
Figure 3:
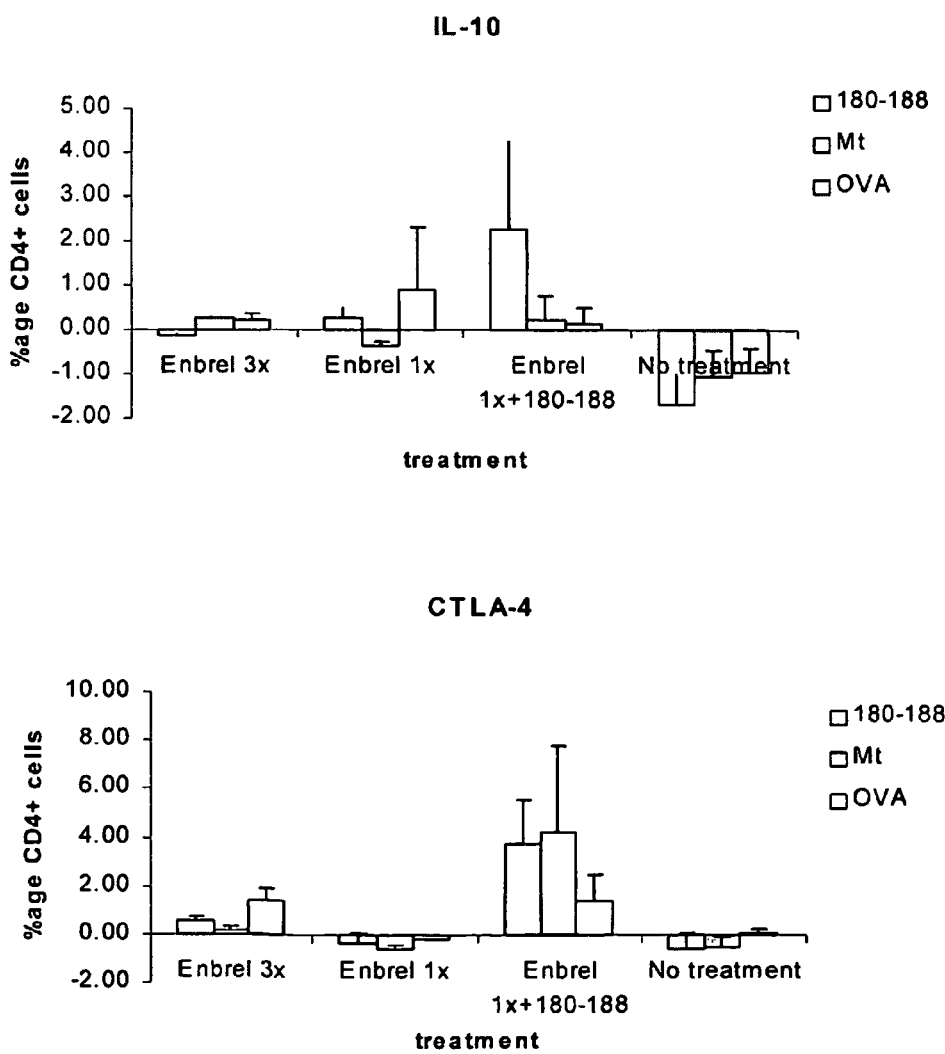
FIG. 3 is a set of bar graphs showing intracellular cytokine production in inguinal lymph nodes (ILN) by FACS analysis. In the first graph is the percentage of CD4+ cells found expressing IL-10. The identification of CD4+ cells which express CTLA-4 and produce IL-10 is a requisite of T regulatory cells.
Figure 4:
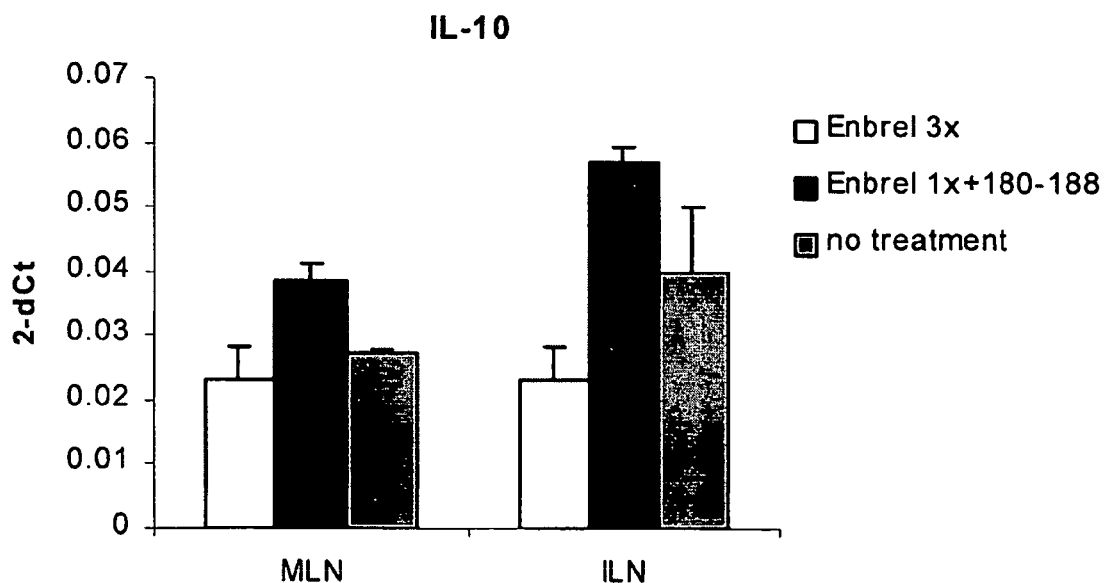
FIG. 4 is a bar graph showing the gene transcription of IL-10 by Taqman technique which is a real time PCR technique.
Figure 5:
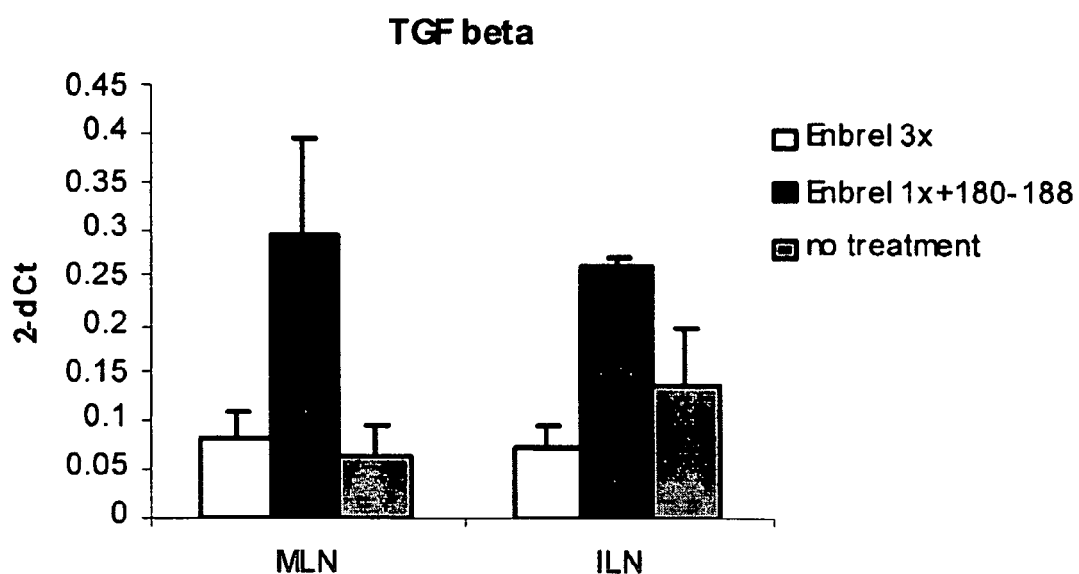
FIG. 5 is a bar graph showing gene transcription of TGFβ by Taqman technique for mandibular lymphocytes (MLN) and (ILN).
Figure 6:
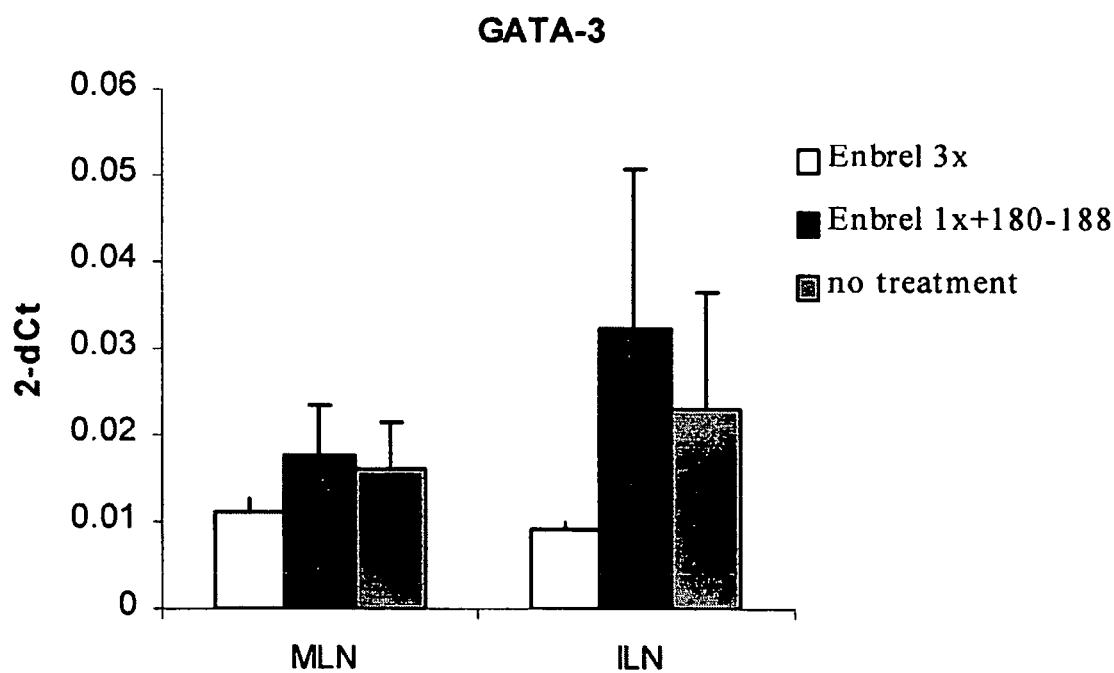
FIG. 6 is a bar graph showing gene transcription of GATA-3 by the Taqman technique.
Figure 7:
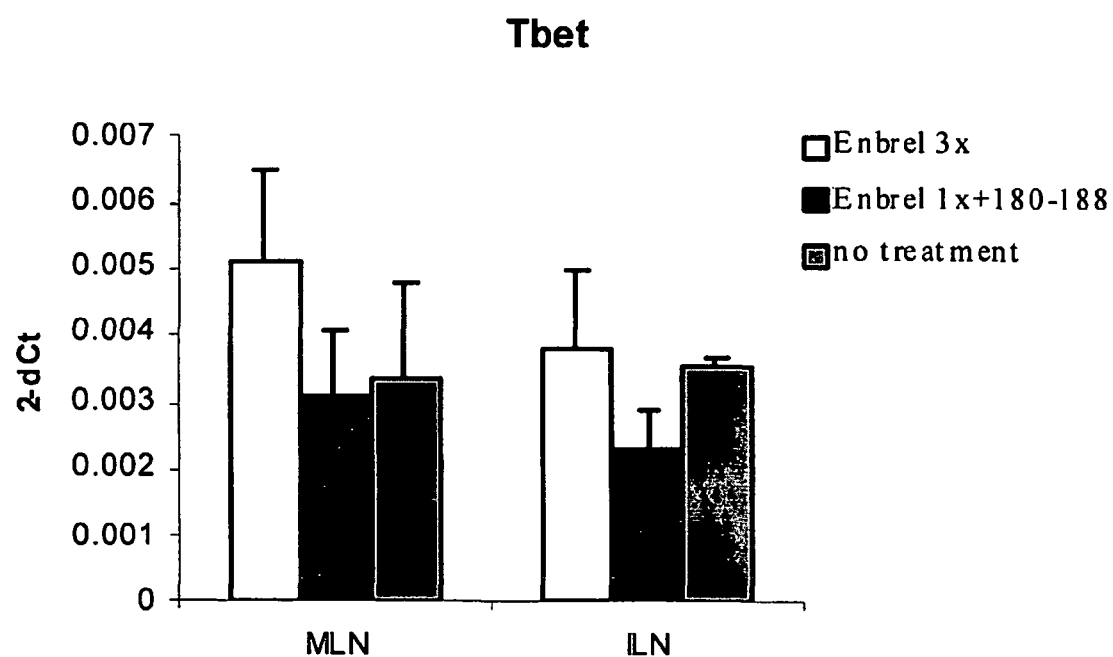
FIG. 7 is a bar graph showing gene transcription of Tbet by Taqman technique.

In FIG. 2 the results of the above regimen show that as of days 22 and 35, MLN are stimulated substantially as shown in the 35 day enbrel/180-188 bar graph. Additional data are provided in FIGS. 3-7. In FIG. 3, intracellular production of (ILN) is shown using FACS analysis. As indicated, the combination therapy sample cells show a substantial stimulation of CD4+ cells as shown by expression of IL-10 or CTLA-4. Likewise, in FIG. 4, gene transcription of IL-10 is markedly increased in the combination treatment sample over the Enbrel alone and no treatment samples. The same is true for gene transcription of TGFβ, and GATA-3 as shown in FIGS. 5 and 6, respectively. However, there is a marked decrease in Tbet expression as shown in FIG. 7. Each of these genes are important in proving efficacy of the combination regimen because Tbet and GATA-3 are gatekeeper genes, which control development of a Th-1 or Th-2 cytokine cascade.

The results show that there is an emergence of antigen-specific proliferation of cells specific for the heat shock peptide 180-188 by day 35, increased gene transcription of IL-10 and TGFβ in MLN and ILN, an increased intracellular production of IL-10, and expression of CTLA-4 in ILN. Therefore, a functional switch towards Th2 by increase in GATA-3, and decrease of Tbet. The overall result is that combination treatment of antigen-specific immunotherapy and anti-TNFα treatment leads to significant reduction of arthritis in Adjuvant Arthritis. Additionally, as one of skill in the art would recognize given the clinical applicability of the above mouse model, there is a correlation between clinical efficacy and generation of regulatory T cells as shown by the proliferation of antigen, IL-10 and TGFβ production and Th2 phenotype stimulation.

Although the invention has been described with reference to the above examples, it will be understood that modifications and variations are encompassed within the spirit and scope of the invention. Accordingly, the invention is limited only by the following claims.

What is claimed is:

1. A method of modulating an immune response in a subject in need thereof comprising:
   a) administering a therapeutically effective amount of the antigen-specific epitope as set forth in SEQ ID NO: 49; and
   b) administering a therapeutically effective amount of a cytokine TNFα or a regulatory effective amount of an agent that affects cytokine activity or expression, wherein the cytokine is TNFα and the agent is an anti-TNFα antibody,
   wherein administration of a) and b) modulates the immune response in the subject.

2. The method of claim 1, wherein the administration is performed by direct administration of a cytokine by mucosal, intravenous, subcutaneous, or intramuscular administration.

3. The method of claim 1, wherein the administration of a cytokine comprises administration of a nucleic acid encoding the cytokine.

4. The method of claim 1 wherein the administration in a) and b) occurs simultaneously.

5. The method of claim 1 wherein the administration in a) and b) occurs sequentially.

6. The method of claim 5, wherein the administration is in varying ratios.

7. The method of claim 1, wherein the cytokine is associated with an inflammatory or a tolerating immune response.

8. The method of claim 7, wherein the inflammatory or tolerating immune response is modulated by an immunomodulatory cytokine.

9. The method of claim 1, wherein the antigen-specific epitope is derived from a heat shock protein.

10. The method of claim 1, wherein the subject has arthritis.

11. The method of claim 1, further comprising ex vivo conditioning of T cells or B cells with soluble cytokines.

12. The method of claim 11, wherein the ex vivo conditioning is performed in the same microenvironment.

13. A method of modulating immune processes and pathogenesis of arthritis comprising:
   administering a combination of antigen-specific epitope and cytokine or anticytokine therapy, wherein the cytokine is TNFα,
   wherein the antigen-specific epitope is the amino acid sequence as set forth in SEQ ID NO: 49, and wherein the administering induces an immune response to arthritis.

14. The method of claim 13, wherein the cytokine is associated with an inflammatory or a tolerating immune response.

15. The method of claim 14, wherein the inflammatory or tolerating immune response is modulated by an immunomodulatory cytokine.

16. The method of claim 13, wherein the antigen-specific epitope is derived from a heat shock protein.

17. A method of treating arthritis in a subject in need thereof comprising:
   a) administering a therapeutically effective amount of an antigen-specific epitope as set forth in SEQ ID NO: 49, wherein administration provides epitope-specific T cell immune modulation; and
   b) administering a therapeutically effective amount of a cytokine or a regulatory effective amount of an agent that affects cytokine activity or expression, wherein the cytokine is TNFα and the agent is an anti-TNFα antibody,
   wherein administration of a) and b) modulates the immune response in the subject, thereby treating the subject.

* * * * *